United States Patent [19]
Orth et al.

[11] Patent Number: 5,534,439
[45] Date of Patent: Jul. 9, 1996

[54] ISOLATED DNA OF HUMAN PAPILLOMAVIRUS TYPE 55 (HPV55)

[75] Inventors: Gerard Orth, Sceaux; Michel Favre; Dina Kremsdorf, both of Paris; Gérard Pehau-Arnaudet, Montreuil, all of France

[73] Assignee: Institut Pasteur, Paris, France

[21] Appl. No.: 240,497

[22] Filed: May 10, 1994

Related U.S. Application Data

[63] Continuation of Ser. No. 951,118, Sep. 25, 1992, Pat. No. 5,342,930, which is a continuation of Ser. No. 351,125, May 12, 1989, abandoned.

[30] Foreign Application Priority Data

May 13, 1988 [FR] France ................................. 88 06486
Jun. 21, 1988 [FR] France ................................. 88 08324

[51] Int. Cl.$^6$ ............................. C12N 15/37; C12N 7/01
[52] U.S. Cl. .................................. 435/320.1; 435/172.3; 435/235.1; 435/252.3; 536/23.1; 536/23.74
[58] Field of Search .................... 435/5, 172.3, 235.1, 435/252.3, 320.1; 536/23.1, 23.74; 436/64

[56] References Cited

U.S. PATENT DOCUMENTS

| | | |
|---|---|---|
| 4,551,270 | 11/1985 | Danos et al. |
| 4,748,109 | 5/1988 | Baird |
| 4,849,331 | 7/1989 | Lorincz |
| 4,849,332 | 7/1989 | Lorincz |
| 4,849,334 | 7/1989 | Lorincz |
| 4,908,306 | 3/1990 | Lorincz |
| 5,057,411 | 10/1991 | Lancaster et al. |

FOREIGN PATENT DOCUMENTS

| | | |
|---|---|---|
| 0192001A2 | 8/1986 | European Pat. Off. |
| 0235004A2 | 9/1987 | European Pat. Off. |
| 0243221A1 | 10/1987 | European Pat. Off. |
| 0342128A1 | 11/1989 | European Pat. Off. |
| 0477972A2 | 4/1992 | European Pat. Off. |
| 0489442A1 | 6/1992 | European Pat. Off. |
| WO87/01375 | 3/1987 | WIPO |
| WO89/09940 | 10/1989 | WIPO |
| WO90/02821 | 3/1990 | WIPO |

OTHER PUBLICATIONS

Barrasso, R., et al., "Lésions Génitales Masculines a Papillomavirus. Intérêt de la Colposcopie," Ann. Dermatol. Venereol., 113: 787–795 (France, 1986).
Beaudenon, S., et al., "A Novel Type of Human Papillomavirus Associated with Genital Neoplasias," Nature, 321: 246–249 (1986).
Coggin, Jr., J. R., and H. zur Hausen, Meeting Report, Workshop On Papillomaviruses and Cancer, Cancer Res., 39: 545–546 (1979).
Cole, S. T., and R. E. Streeck, "Genome Organization and Nucleotide Sequence of Human Papillomavirus Type 33, Which Is Associated with Cervical Cancer," J. Virol., 58(3): 991–995 (1986).
Cole, S. T., and O. Danos, "Nucleotide Sequence and Comparative Analysis of the Human Papillomavirus Type 18 Genome: Phylogeny of Papillomaviruses and Repeated Structure of the E6 and E7 Gene Products," J. Mol. Biol., 193(4): 599–608 (1987).
de Villiers, E.–M., "Heterogeneity of the Human Papillomavirus Group," J. Virol., 63(11): 4898–4903 (1989).
Durst, M., et al., "A Papillomavirus DNA from a Cervical Carcinoma and its Prevalence in Cancer Biopsy Samples from Different Geographic Regions," Proc. Natl. Acad. Sci. USA, 80: 3812–3815 (1983).
Favre, M., et al., "Human Papillomavirus Type 49, a Type Isolated from Flat Warts of Renal Transplant Patients," J. Virol., 63(11): 4909 (1989).
Favre, M., et al., "Human Papillomavirus (HPV) Type 50, a Type Associated with Epidermodysplasia Verruciformis (EV) and Only Weakly Related to Other EV–Specific HPVs," J. Virol., 63(11): 4910 (1989).
Gissmann, L., et al., "Human Papillomavirus Types 6 and 11 DNA Sequences in Genital and Laryngeal Papillomas and in Some Cervical Cancers," Proc. Natl. Acad. Sci. USA, 80: 560–563 (1983).
Kawashima, M., et al., "Characterization of a New Type of Human Papillomavirus Found in a Lesion of Bowen's Disease of the Skin," J. Virol., 57(2): 688–692 (1986).
Kremsdorf, D., et al., "Biochemical Characterization of Two Types of Human Papillomaviruses Associated with Epidermodysplasia Verruciformis," J. Virol., 43(2): 436–447 (1982).
Kremsdorf, D., et al., "Human Papillomaviruses Associated with Epidermodysplasia Verruciformis. II. Molecular Cloning and Biochemical Characterization of Human Papillomavirus 3a, 8, 10, and 12 Genomes," J. Virol., 48(2): 340–351 (1983).

(List continued on next page.)

*Primary Examiner*—Christine M. Nucker
*Assistant Examiner*—Laurie Scheiner
*Attorney, Agent, or Firm*—Finnegan, Henderson, Farabow, Garrett & Dunner

[57] ABSTRACT

The invention relates to papillomavirus probes derived from new DNA-HPVs deposited with the C.N.C.M. on May 6, 1988, under the following filing numbers:

| | |
|---|---|
| PGEM 4 HPV49: | I-754 |
| PSP 65 HPV50: | I-755 |
| PSP 64 HPV54: | I-756 |
| PGEM 4 HPV55A: | I-757 |
| PGEM 4 HPV55B: | I-758 |

These probes can be used for in vitro detection of:
- in the case of HPV49: warts of the skin (in particular, common and plantar warts) and the differential diagnosis of epidermodysplasia verruciformis,
- in the case of HPV50: epidermodysplasia verruciformis, intraepithelial neoplasias and cutaneous cancer,
- in the case of HPV55_: genital neoplasias and cancers of the uterine cervix,
- in the case of HPV55_: genital neoplasias and cancers of the uterine cervix, condylomas and papillomas.

3 Claims, 3 Drawing Sheets

OTHER PUBLICATIONS

Kremsdorf, D., et al., "Molecular Cloning and Characterization of the Genomes of Nine Newly Recognized Human Papillomavirus Types Associated with Epidermodysplasia Verruciformis," J. Virol., 52(3): 1013–1018 (1984).

Lörincz, A. T., et al., "Human Papillomavirus Type 56: a New Virus Detected in Cervical Cancers," J. gen. Virol., 70: 3099–3104 (1989).

Nuovo, G. J., et al., "Isolation of a Novel Human Papillomavirus (Type 51) from a Cervical Condyloma," J. Virol., 62(4): 1452–1455 (1988).

Parent, B., and B. Huynh, "Les dysplasies du col utérin," J. Gynecol. Obstet. Biol. Reprod., 15: 941–947 (1986).

Pouwels, P. H., et al., Cloning Vectors, A Laboratory Manual, VIII: 1–3,5–7 (Elsevier, Amsterdam, 1985).

Schwartz, E., et al., "DNA Sequence and Genome Organization of Genital Human Papillomavirus Type 6b," The EMBO Journal, 2(12): 2341–2348 (1983).

Seedorf, K., et al., "Human Papillomavirus Type 16 DNA: Expression of Open Reading Frames in E. coli," UCLA Symposium on Molecular and Cellular Biology, New Ser., vol. 32: Papillomaviruses: Molecular and Clinical Aspects: 391–396 (Alan R. Liss, Inc., 1985).

Seedorf, K., et al., "Human Papillomavirus Type 16 DNA Sequence," Virol., 145: 181–185 (1985).

ISOLATED DNA OF HUMAN PAPILLOMAVIRUS TYPE 55 (HPV55)

This is a continuation of application Ser. No. 07/951,118, filed Sep. 25, 1992, now U.S. Pat. No. 5,342,930 which is a continuation of Ser. 07/351,125, May 12, 1989, abandoned.

The invention relates to the DNAs of papillomaviruses (HPV49, HPV50, HPV54, HPV55) or variants of these papillomaviruses, and more particularly to probes derived from these papillomaviruses (HPV49, HPV50, HPV54, HPV55). The invention also relates to products genetically and immunologically related to these papillomaviruses as well as to procedures making use of these various products for the in vitro diagnosis of papillomavirus infections and, in the case of some of them, for vaccination against these same papillomaviruses or variants of papillomaviruses.

By the expression "product genetically or immunologically related to a papillomavirus" should be understood the various products derived from its original DNA whether they be corresponding RNAs or recombinant DNAs containing all or part of this original DNA as well as the "immunological" products resulting from the expression of these DNAs, where appropriate recombinant DNAs, in competent cell hosts. Thus, they are polypeptides resulting from the transcription and translation of all or part of the different open reading frames of the original DNA. They also include antibodies induced in vivo by the said polypeptides.

The expression "papillomavirus" covers a large number of viruses having in common the role of being held responsible for several forms of viral infections ranging from relatively benign warts of the skin and mucous membranes to hyperplasias capable of degenerating into intra-epithelial neoplasias and cutaneous cancers. Among papillomavirus infections, mention should also be made more particularly of cutaneous warts (in particular common warts and plantar warts epidermodysplasia verruciformis, plane or intermediary skin warts, intra-epithelial neoplasias and cutaneous cancers, the cancers of the epidermodysplasia verruciformis, genteel neoplasias and cancer of the uterine cervix, condylomas and papillomas.

A certain number of types of papillomavirus have already been described. As examples, mention should be made of those described in French patent No. 84.18369/2.578.267 and its certificates of addition No. 85.07073/2.581.655 and No. 86.01425/2.593.828, all relating to new types and subtypes of papillomaviruses which have been isolated from warts or disseminated macular lesions, among which some are more likely than others to give rise to the early development of cancers of the skin in patients who are infected by them.

The importance of immune factors and the major role of various types of human papillomaviruses (HPV) are also known, these factors being additional to the role already described in the literature of various genetic factors and actinic radiations in the pathogenesis of papillomavirus infections.

The invention of the French patent and of its certificates of addition derived from observations which have been made with regard to the relative behaviour of a large number of newly isolated papillomaviruses, the essential genomic characteristics of which have been defined.

Several types and subtypes of new papillomaviruses have been described in the French patent and in the certificates of addition. The same is true for the utilization of the DNAs of these new papillomaviruses, taken individually or in combination among themselves and/or with the DNAs of previously known HPVs, in more refined in vitro diagnostic techniques.

The general observation was made in the French patent that the papillomaviruses, although differing very much among themselves, had genomes having sizes of the order of 7000–8000 base pairs. Furthermore, their genomes may nonetheless present certain degrees of homology, measured as percentages of homology, in hybridization assays carried out under "non stringent" conditions or, under "stringent" conditions of hybridization.

It has been said that the papillomaviruses which show percentages of homology of less than 50% under stringent conditions belong to different types. Viruses for which percentages of homology higher than 50% are observed under the same stringent conditions are considered to belong to the same type. They may form different subtypes within this same type.

The hybridization assay under non-stringent conditions comprises contacting DNAs derived from two isolates of virus under the conditions described by HEILMAN C. A. et al., 1980, J.Virol., 36, 395–407, and CROISSANT et al., 1982, C.R. Acad. Sc. Paris, 294, 581–586 (heteroduplex molecules). In particular, the "non-stringent" conditions comprise contacting DNA of the papillomavirus under study, a variant of this papillomavirus or a clone of this DNA, with the DNA of the reference papillomavirus at a temperature lower than about 40° C. of the melting temperature (Tm) of the hybrids.

The hybridization assays under stringent conditions involve DNAs derived from two isolates of virus under the conditions described by KREMSDORF, D. et al. (1982), J. Virol. 43:436–447 and 1983, J. Virol. 48:340–351) and Davis, R. W. et al., 1971, Methods Enzymol., 21, 413–418 (heteroduplex molecules). In particular, the "stringent" conditions comprise contacting DNA of the papillomavirus under study, a variant of this papillomavirus, or of a clone of this DNA, in contact with the DNA of the reference papillomavirus at a temperature lower than about 20° C. of the melting temperature (Tm) of the hybrids.

Several viruses have been described in the French patent and in the certificates of addition. Similarly, genetic recombinants have been described containing all or part of the genomes of these viruses (designated DNA-HPVs). The invention of the main patent and of the certificates of addition consequently related to the DNA-HPVs having in common sizes ranging between 7000 and 8000 base pairs and characterized by restriction maps occurring in the drawings of these patents and certificates of addition. In particular, the drawings provide the restriction maps of DNA-HPVs obtained from the papillomaviruses and which are designated HPV2d, HPV10b, HPV14a, HPV14b, HPV15, HPV17a, HPV17b, HPV19, HPV20, HPV21, HPV22, HPV23, HPV24, HPV28, HPV29, HPV32 (formerly HPV31), HPV33 (formerly HPV32 or HPV-IP2), HPV34 (formerly HPV-IP3), HPV36 (formerly HPV-IP4), HPV39 (formerly IP5) and HPV42 (formerly IP6).

The invention of the French patent and of its certificates of addition also related to mixtures or "cocktails" of DNA-HPVs isolated from the papillomaviruses which were new at that time and/or from papillomaviruses already known at the filing dates of the corresponding titles, or hybridization probes containing the DNA-HPVs. The probes may be used more efficaciously for the diagnosis of various categories of infections, and even of the levels of risks which accompany the discovery of specific papillomaviruses in a patient. The discovery of new papillomaviruses or of DNAs which are derived from them thus offers the possibility of carrying out more refined diagnoses, in particular, of a greater discrimination of the various categories of infections which can be imputed to various types of papillomaviruses or which are capable of developing under the influence of these latter types and, within a class of specific infections, to provide a better prognosis of the degree of risk of these latter infections being transformed into more serious diseases.

In this respect, the present invention relates to newly isolated papillomaviruses, the genomic DNAs which can be extracted from them, or fragments of these genomic DNAs as well as novel hybridization probes which can be formed from these DNA-HPVs or fragments of DNA-HPVs. It also relates to all of the variants of these papillomaviruses, belonging respectively to the same subtypes, thus capable of hybridizing with the corresponding papillomaviruses identified below by reference to their restriction maps under stringent conditions.

The DNA-HPVs according to the present invention, designated hereafter as HPV49, HPV50, HPV54, HPV55 are characterize by the restriction maps presented in the appended figures (FIGS. 1 to 4).

The physical maps give the position of cleavage sites by various restriction endonucleases. The origin of each map is constituted by a unique cleavage site. The distances of the other sites with respect to the origin are expressed in percentages of the length of the genome.

The invention also relates to new "cocktails" of probes comprising some of the "cocktails" of probes already described in the French patent or in the certificates, of addition, supplemented, however, with a probe derived from one of the papillomaviruses according to the present application and consequently, the invention relates to improved diagnostic "kits".

The hybridization probes constructed from the genomes of HPV (HPV49, HPV50, HPV54, HPV55) are particularly useful for in vitro diagnosis and/or screening under the conditions which were described in the French patent and in the certificates of addition, and which will be described again later. The news types of papillomaviruses and the diagnoses they may be used for are delineated below. In the case of HPV49: cutaneous warts (in particular, common warts and plantar warts) and the differential diagnosis of epidermodysplasia verruciformis, In the case of HPV50: the epidermodysplasia verruciformis, intra-epithelial neoplasias and cutaneous cancers, In the case of HPV54: genital neoplasias and cancers of the uterine cervix In the case of HPV55: genital neoplasias and cancers of the uterine cervix, condylomas and papillomas.

These hybridization probes are advantageously incorporated into "cocktails" for the diagnosis of diseases of the same type to which we will return later. In this respect, reference will again be made to the French patent and to the certificates of addition in which the restriction maps of some other constituents of these diagnostic mixtures are presented. In this respect, the French patent and the certificates of addition must be considered as constituting part of the present description as far as the identification of the other DNA-HPVs implicated in the compositions of these "cocktails" is concerned.

The invention also relates to fragments of each of the preceding DNA-HPVs or to DNA-HPVs capable of hybridizing with them, in particular under stringent conditions. Similarly, it relates to recombinant DNAs containing all or part of the DNA-HPVs mentioned above, and more particularly to the recombinant DNAs containing fragments corresponding to the genes E1, E2, E6-E7, L1, L2 and the non coding intergenic region. It also relates to probes which may be constituted from these DNA-HPVs or from corresponding fragments, and the in vitro diagnostic procedures making use of the said probes or the mixtures containing them.

The preparations of the viral DNAs were extracted according to the techniques described below.

In what follows, the conditions under which each of the papillomaviruses according to the invention was isolated are described, and then the conditions under which the DNA-HPV was obtained from the particular papillomavirus are described.

MOLECULAR CLONING AND CHARACTERIZATION OF A NEW TYPE OF HPV (HPV 49) FOUND IN A WART IN AN IMMUNOSUPPRESSED PATIENT

A new type of HPV has been demonstrated in the DNA extracted from an intermediate wart on the hands of a renal transplant patient by hybridization, under non-stringent conditions, with a radioactive probe specific for the DNA of HPV5. A study of the sensitivity of the DNA of this HPV to restriction enzymes has shown that the endonuclease EcoRI cleaves the viral DNA once. After treatment of the tumor DNA with the endonuclease EcoRI, the products of digestion were inserted by EcoRI into the DNA of the plasmid vector pGem4. The recombinant plasmids having integrated the DNA of the new HPV were selected by the technique of colony hybridization (Benton and Davis) by using a specific radioactive DNA probe of HPV5 under non-stringent conditions. A recombinant plasmid containing the totality of the viral sequences was isolated. The cleavage of the DNA of the recombinant plasmid and the preparation of the DNA extracted of the wart by the mixture of the endonucleases EcoRI and HindIII gives rise to the same four fragments of viral DNA, the molecular weight of which corresponds to that of a papillomavirus genome (about 8 kilobases).

Figure 1:
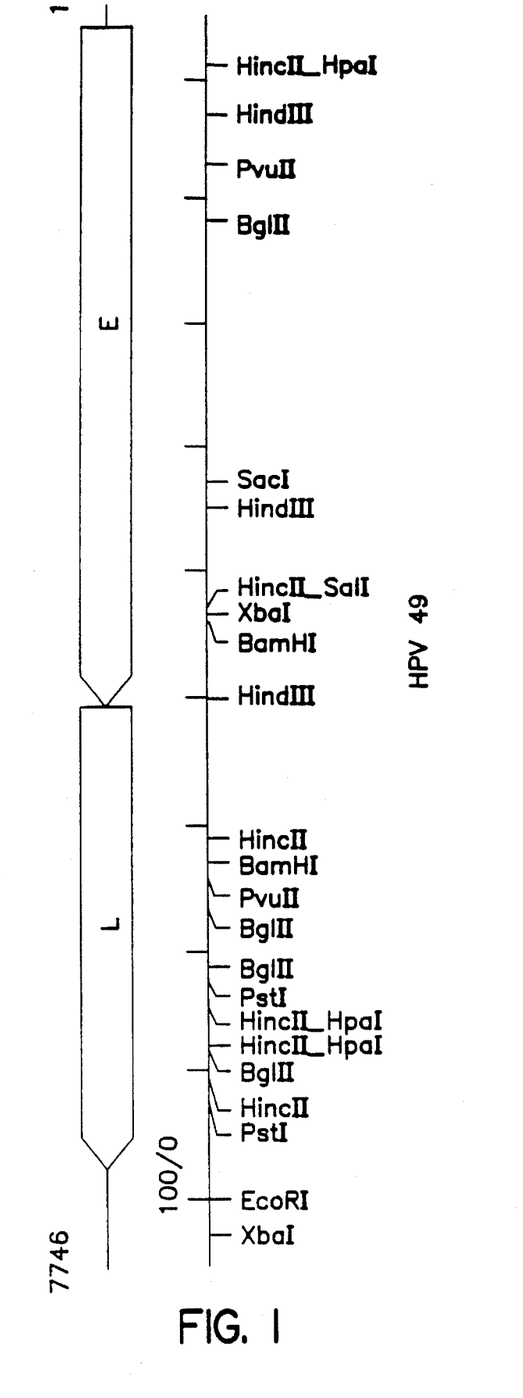
FIG. 1 corresponds to a restriction map of HPV49. The viral DNA was cleaved once by the endonuclease EcoRI to linearize the viral DNA. The origin of the map is constituted by this unique cleavage site. The map gives the position of cleavage sites by various restriction endonucleases. The distances of the other sites with respect to the origin is expressed in percentages of the length of the genome in Table 1.
Figure 2:
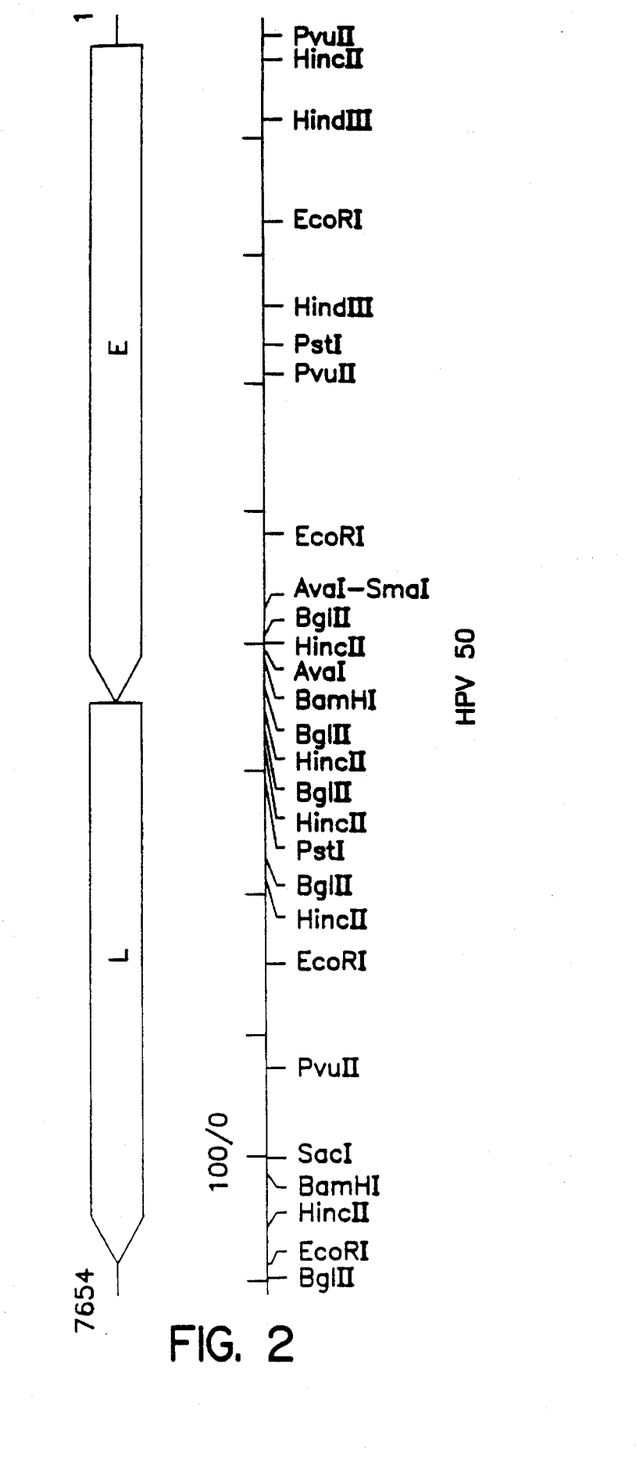
FIG. 2 corresponds to a restriction map of HPV50. The viral DNA was cleaved once by the restriction endonuclease EcoRI. This site constitutes the origin of the restriction map. The map gives the position of cleavage sites by various restriction endonucleases. The distances of the other sites with respect to the origin are expressed in percentages of the length of the genome in Table 2.
Figure 3:
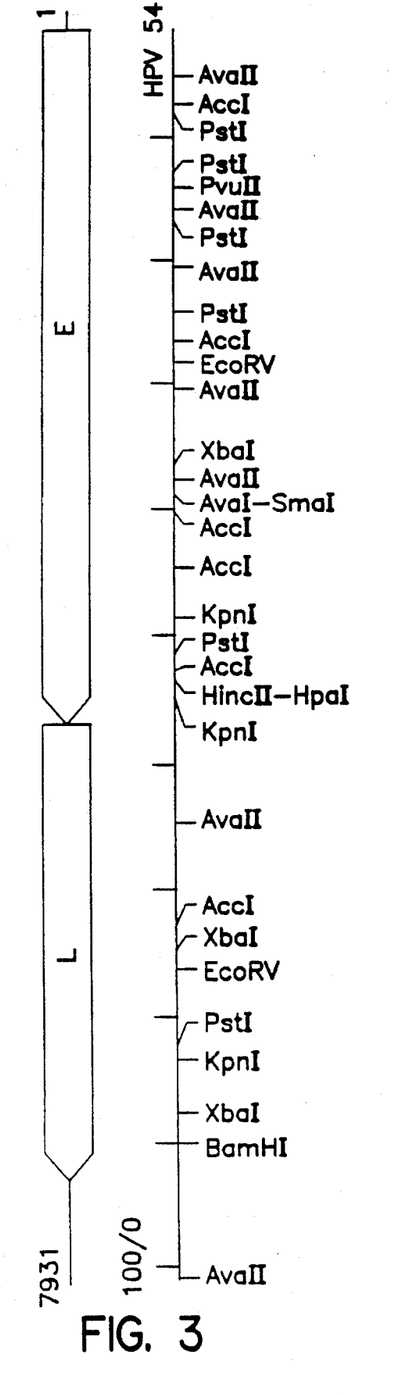
FIG. 3 corresponds to a restriction map of HPV54. The viral DNA was cleaved once with the endonuclease BamHI. This cleavage site constitutes the origin of the restriction map. The map gives the position of cleavage sites by various restriction endonucleases. The distances of the other sites with respect to the origin are expressed in percentages of the length of genome in Table 3.
Figure 4:
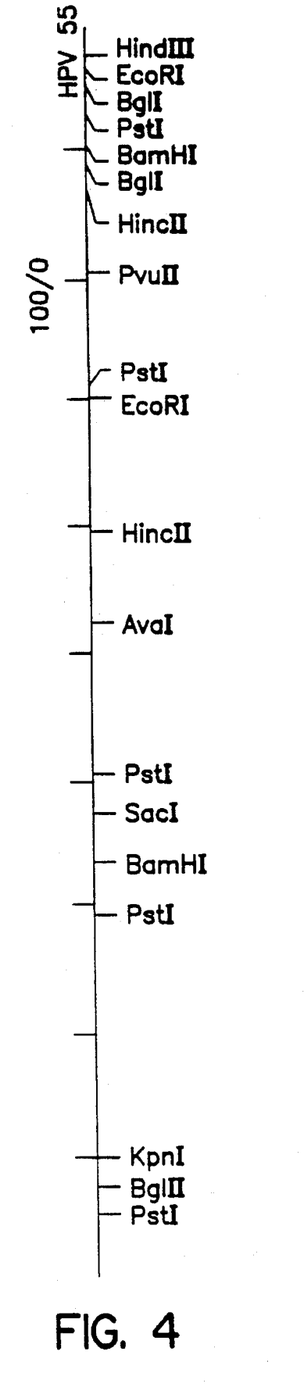
FIG. 4 corresponds to a restriction map of HPV55. The viral DNA was first cleaved twice by the endonuclease EcoRI, producing two fragments of DNA of molecular weight 5.65 and 2.15 kb. A comparison of the DNA of HPV55 and the DNA of HPV11 enabled the alignment of the physical map of the DNA of HPV55 with the genetic map of HPV11 to define the position of the two fragments of HPV55. The physical map gives the position of cleavage sites by various restriction endonucleases. The relative distances of the other sites are expressed in percentages of the length of the genome in Table 4.

A restriction map of the DNA of the new HPV has been constructed from the study of the sensitivity of this DNA to 18 restriction endonucleases. Twenty-seven cleavage sites have been localized (FIG. 1). This map is different from that of all the HPV isolated up to the present. The degree of homology between the DNA of the new HPV and the DNA of the HPVs identified up to the present was analyzed by blot hybridization experiments under more or less stringent conditions by using a radioactive DNA probe specific for the new HPV. A sequence homology between the DNA of the new HPV and the DNA of the hitherto identified HPVs was detected only under non-stringent conditions of hybridization. The most extensive cross-hybridization was observed with the DNA of the HPVs specifically associated with epidermodysplasia verruciformis. The new virus characterized from a wart of an immunosuppressed patient thus constitutes a new type of HPV designated HPV49.

Electron microscopic analysis of the heteroduplex molecules formed between the DNA of the HPV49 and the DNA of the HPV5 has made it possible to define the theoretical position of the different genes on the DNA of the HPV49. Similarly, the establishment of the nucleotide sequence of a DNA fragment of the HPV49 has made it possible to align the physical map of the DNA of the HPV49 with the genetic map of the HPV5.

The pathogenicity of the HPV49 was investigated with the aid of radioactive probes prepared from the DNA of this virus. The HPV49 was investigated in warts taken from immunosuppressed patients (27 cases), butchers (26 cases) or in the general population (21 cases), in benign lesions of 31 patients suffering from EV, in 18 cases of keratoacanthoma, in 20 cases of cutaneous Bowen's disease, in 25 cases of actinic keratosis, in 25 cases of basal cell carcinoma, in 23 cases of squamous cell carcinoma. HPV49 was found in two other immunosuppressed patients.

Although rare, HPV49 constitutes an additional type of cutaneous HPV associated with warts. It is advisable to incorporate it in any DNA mixture of HPVs destined for the preparation of molecular probes with a view to the diagnosis of types of HPV associated with warts in particular in immunosuppressed subjects.

In the table which follows are specified the putative locations of the principal genes and of the intergenic region of HPV49 on the map of this genome:

TABLE 1

|  | Coordinates of the ends (%) | |
| --- | --- | --- |
|  | 5' | 3' |
| E6–E7 | 2 | 12, 5 |
| E1 | 11 | 34, 5 |
| E2 | 34 | 54 |
| L2 | 54, 5 | 76 |
| L1 | 76 | 97 |
| Intergenic region | 97 | 2 |

MOLECULAR CLONING AND CHARACTERIZATION OF A NEW TYPE OF HPV ASSOCIATED WITH LESIONS OF ACTINIC KERATOSIS (HPV50)

A new type of HPV has been demonstrated in the DNA extracted from the mixture of lesions of actinic keratosis taken from a patient suffering from epidermodysplasia verruciformis (EV) by hybridization under non-stringent conditions with a specific radioactive DNA probe of HPV5. This preparation of tumor DNA had previously been shown to contain the DNAs of the HPVs5, 20, 23 and 36. A DNA fragment of about 1.9 Kb, corresponding to the DNA of the new HPV, was observed after digestion of the DNA extracted from the lesions by the restriction endonuclease EcoRI. The tumor DNA was treated with the enzyme EcoRI, and the products of digestion were inserted at the EcoRI site in the DNA of the bacteriophage λGt10 making it possible to clone DNA fragments, the size of which is less than 7 kb. After encapsidation of the recombinant DNA and infection of *Eacherichia coli* K12 (strain C600) bacteria, the recombinant bacteriophages having inserted the DNA fragment of 1.9 kb were selected by means of the technique of plaque hybridization by using a radioactive HPV5 DNA probe under non-stringent conditions. Several recombinant bacteriophages were isolated and shown to contain the DNA fragment of 1.9 Kb. This DNA fragment was excised from the phage DNA sequences and recloned in the plasmid SP65. A radioactive probe prepared from the DNA fragment of 1.9 Kb, excised and purified from the plasmid sequences, showed no cross-hybridization under stringent conditions with the DNAs of the HPVs5, 20, 23 and 36. On the contrary, this probe has made it possible to demonstrate a DNA fragment of 1.9 Kb in the DNA extracted from the lesions treated with the enzyme EcoRI as well as HPV DNA molecules supercoiled form I (circular supercoiled) and form II (open circles) in the untreated tumor DNA. A study of the sensitivity of the DNA of this new HPV to several restriction enzymes has shown that the enzyme SacI cleaves the viral DNA once. After digestion of the tumor DNA by the enzyme SacI, the DNA molecules of 8 Kb (size of the genome of a HPV) were purified by centrifugation in a sucrose gradient, then inserted at the SacI site in the DNA of the plasmid SP65. The recombinant plasmids having integrated the DNA of the new HPV were selected by means of the colony hybridization method by using a radioactive DNA probe specific for the 1.9 Kb fragment under stringent conditions. Several recombinant plasmids containing the totality of the viral sequences were isolated. The cleavage of the DNA of the recombinant plasmids by the endonuclease SacI gives rise to a fragment of 8 Kb hybridizing with the DNA fragment of 1.9 Kb under stringent conditions. The cleavage of the DNA of the recombinant plasmids and of the DNA preparation extracted from the lesions by a mixture of the enzymes SacI and PvuII, generate the same four fragments, the total molecular weight of which corresponds to that of a papillomvirus genome (8 Kb).

A restriction map of the DNA of the new HPV has been constructed from a study of the sensitivity of this DNA to 16 restriction enzymes. Twenty-eight cleavage sites were localized. The map thus established is different from that of the genomes of the HPVs identified hitherto. The sequence homology between the DNA of the new HPV and the DNAs of the HPVs characterized up to now was analyzed by blot hybridization experiments carried out under stringent or non-stringent conditions. No sequence homology was revealed under stringent conditions. On the contrary, under non-stringent conditions, a significant, although weak, cross-hybridization was observed only between the DNA of this new HPV and the DNAs of the HPVs specific for the EV. The virus isolated from actinic keratosis lesions, observed in a patient suffering from EV, thus constitutes a novel type of HPV, designated HPV50.

The comparative analysis of the nucleotide sequence of the HPV8 and a small region of the genome of the HPV50 has made it possible to align the physical map of the HPV50 with the genetic map of the HPV8 and define the theoretical position of the different genes carried by the DNA of the HPV50.

The use of radioactive probes prepared from the DNA of the purified HPV50 has made it possible to determine the pathogenicity of this virus. The HPV50 has not been found in warts observed in subjects of the general population (22 cases analysed), in immunosuppressed patients (27 cases), and in butchers (26 cases), in 18 cases of keratoacanthoma, in 20 cases of cutaneous Bowen's disease, in 25 cases of actinic keratosis, in 24 cases of basal cell carcinoma and in 22 cases of squamous cell carcinoma. On the other hand, the DNA of the HPV50 has been detected in the DNA extracted from scrapings of benign lesions in three patients out of the 31 studied who were suffering from EV.

The HPV50 thus constitutes an additional type of cutaneous HPV associated with EV. It is advisable to incorporate it into any mixture of DNA-HPV destined for the preparation of molecular probes with a view to the diagnosis of the types of HPV associated with EV.

In the table which follows are specified the putative locations of the principal genes and the intergenic region of the HPV50 on the map of this genome:

TABLE 2

| | Coordinates of the ends (%) | |
|---|---|---|
| | 5' | 3' |
| E6-E7 | 1, 8 | 12, 6 |
| E1 | 10, 2 | 36 |
| E2 | 35 | 54, 8 |
| L2 | 55, 8 | 76, 2 |
| L1 | 75, 2 | 96, 6 |
| Intergenic region | 96, 6 | 1, 8 |

MOLECULAR CLONING AND CHARACTERIZATION OF A NEW TYPE OF HPV FOUND IN A BUSCHKE LOEWENSTEIN TUMOR (HPV54)

A new type of HPV has been demonstrated in the DNA extracted from a Buschke Loewenstein tumor of the penis by hybridization under non-stringent conditions with a radioactive probe specific for HPV18. A study of the sensitivity of the DNA of this HPV to several restriction endonucleases has shown that the endonuclease BamHI cleaves the viral DNA once. After digestion of the DNA extracted from the tumor by means of the endonuclease BamHI, the fraction containing DNA molecules of 8 Kb (the size of a HPV genome) was purified by centrifugation in a sucrose gradient. The molecules of 8 Kb were inserted at the BamHI site in the DNA of the bacteriophage Lambda 147.1. After encapsidation of the recombinant DNA and transfection of the host bacteria (*Escherichia coli*, strain LA101), the recombinant bacteriophages having inserted the DNA of the new HPV were selected by means of the plaque hybridization technique (Benton and Davis) by using a radioactive DNA probe specific for HPV18 under non-stringent conditions. Several recombinant bacteriophages containing the totality of the viral sequences were isolated. The cleavage of the DNA of the recombinant bacteriophages and the preparation of the DNA extracted from the tumor by a mixture of the endonucleases BamHI and PstI gives rise to the same fragments, the total molecular weight of which corresponds to that of a HPV genome. The DNA of the new HPV was excised from phage DNA sequences and recloned in the plasmid SP64.

A restriction map of the DNA of the new HPV was constructed from a study of the sensitivity of this DNA to 20 restriction endonucleases. Thirty-three sites were localized. This map is different from that of all of the HPVs hitherto isolated. The degree of homology between the DNA of the new HPV and the DNA of the known types of HPV was analyzed by bloc hybridization experiments under stringent or non-stringent conditions by using a radioactive DNA probe specific for the new HPV. Only limited sequence homology was observed under non-stringent conditions of hybridization. A slightly more extensive cross-hybridization was detected between the DNA of the new HPV and the DNAs of the HPVs associated with the lesions of the mucous membranes. The virus isolated from the Buschke Loewenstein tumor thus constitutes a new type of HPV, HPV54.

The analysis under the electron microscope of heteroduplex molecules formed between the DNA of the HPV54 and the DNA of the HPV16 as well as the determination of the nucleotide sequence of a DNA fragment of the HPV54 have made it possible to align the physical map of HPV54 with the genetic map of HPV16 and to define the theoretical position of the different genes carried by the DNA of HPV54.

Attempts were made to detect the DNA of HPV54 in DNA preparations obtained from genital lesions of 179 patients. HPV54 was not found in 67 specimens of condyloma acuminatum, 10 specimens of Buschke Loewenstein tumors, 10 specimens of bowenoid papulosis, 17 specimens of Bowen's disease, 40 specimens of invasive carcinoma and 28 specimens of intra-epithelial neoplasias of the cervix.

HPV54 constitutes a new type of HPV very weakly related to the genital HPVs characterized up to the present. It is advisable to incorporate it in any mixture intended for the preparation of molecular probes with a view to the diagnosis of the types of HPVs associated with genital lesions.

In the table which follows are specified the putative locations of the principal genes and of the intergenic region of HPV54 on the map of this genome:

TABLE 3

| | Coordinates of the ends (%) | |
|---|---|---|
| | 5' | 3' |
| E6-E7 | 1, 8 | 10, 8 |
| E1 | 10, 8 | 35, 6 |
| E2 | 34, 5 | 48, 7 |
| L2 | 52, 3 | 71, 5 |
| L1 | 69, 9 | 90, 5 |
| Intergenic region | 90, 5 | 1, 8 |

MOLECULAR CLONING AND CHARACTERIZATION OF A NEW TYPE OF HPV ASSOCIATED WITH CONDYLOMATA ACUMINATA (HPV55)

A new type of HPV has been demonstrated in the DNA extracted from a condyloma acuminatum of the penis by hybridization under non-stringent conditions with a radioactive DNA probe specific for HPV6. A study of the sensitivity to several restriction endonucleases has shown that the DNA of this HPV is cleaved twice by the endonuclease EcoRI giving rise to two fragments of DNA of molecular weight 5.65 and 2.15 Kilobases (Kb), the sum of which (78 Kb) corresponds to the size of a HPV genome. After digestion of the tumor DNA by the enzyme EcoRI, the DNA framents were inserted at the EcoRI site in the DNA of the bacteriophage lambda gt10. After encapsidation of the recombinant DNA and infection of Escherichia coli K12 (strain C600) bacteria, the recombinant bacteriophages containing the subgenomic fragments of the new HPV were selected by means of the plaque hybridization technique (Benton and Davis) by using a DNA probe of HPV6 under non-stringent conditions of hybridization. Several recombinant bacteriophages containing one or other of the two fragments corresponding to the genome of the new HPV have been characterized. The treatment of the tumor DNA extracted from the lesions and the recombinant bacteriophages by the endonuclease EcoRI give rise to the two expected fragments of 5.65 and 2.15 Kb. The two fragments were excised from the phage DNA sequences and recloned in the plasmid pGem4. A restriction map of the DNA of the new HPV was constructed from a study of the sensitivity of this DNA to 15 restriction endonucleases. Nineteen cleavage sites were localized. This map is different from that of all of the HPVs characterized up to the present. The sequence homology between the DNA of the new HPV and the DNA of the known HPVs was analyzed by blot hybridization experiments carried out under stringent conditions by using a radioactive DNA probe specific for the new HPV. A partial hybridization was observed with the DNA of the new HPV and the DNA of HPV13 and a more limited cross-hybridization was detected with the DNAs of the HPVs6 and 11. The degree of homology of DNA was assessed by hybridization experiments in liquid phase at saturation, followed by digestion of the hybrids by nuclease S1; it was estimated to be 20, 10 and 10% between the DNA of the new HPV and the DNA of the HPVs13, 6 and 11, respectively. The virus isolated from a condyloma of the penis thus constitutes a new type of HPV, HPV55.

Analysis under the electron microscope of heteroduplex molecules formed between the DNA of HPV55 and the DNA of the HPV11 and the establishment of the nucleotide sequence of a DNA fragment of HPV55 has made it possible to align the physical map of the DNA of HPV55 with the genetic map of HPV11 and to define the theoretical position of the different genes carried by the DNA of HPV55.

The use of radioactive probes prepared from the DNA of the purified HPV55 has made it possible to study the pathogenicity of this virus. The DNA of HPV55 could be detected only in an anal condyloma of another patient out of the 67 cases studied. HPV55 was not detected in the DNA extracted from other types of genital lesions obtained from 96 additional patients.

Although rare, HPV55 must be incorporated in any mixture of HPV intended for the preparation of probes with a view to the diagnosis of HPV types associated with genital lesions.

In the table which follows are specified the putative locations of the principal genes and the intergenic region of HPV55 on the map of this genome:

TABLE 4

| | Coordinates of the ends (%) | |
|---|---|---|
| | 5' | 3' |
| E6–E7 | 1, 3 | 10, 4 |
| E1 | 9 | 35 |
| E2 | 34 | 48, 2 |
| L2 | 55, 6 | 72, 9 |
| L1 | 71, 4 | 91, 7 |
| Intergenic region | 91, 7 | 1, 3 |

In a general way, the invention thus also relates to any recombinant DNA containing the above-mentioned DNA-HPV or fragments of this DNA-HPV, in particular hybridization probes formed from these recombinant DNAs for the detection of an infection by the papillomavirus or a variant of this papillomavirus according to the invention. These probes may be either labelled themselves or be modified at certain nucleotides, in particular, to couple them directly or indirectly to a distinct marker.

The procedure according to the invention for in vitro diagnosis of a biological sample to be tested of an infection by a papillomavirus (HPV49, HPV50, HPV54, HPV55) or by a variant, is thus characterized by contacting a probe, such as that defined above with the nucleic acids of this sample, previously contacted, with the probe if necessary, preferably under stringent conditions of hybridization, and by the detection of the hybrid formed between the viral DNA under study and possibly present in the sample and the said probe.

The procedure according to the invention is particularly advantageous for the in vitro detection of
  HPV49: in cutaneous warts (in particular, common and plantar warts) and the differential diagnosis of epidermodysplasia verruciformis,
  HPV50: in epidermodysplasia verruciformis, intra-epithelial neoplasias and cutaneous cancers,
  HPV54: in genital neoplasias and cancers of the uterine cervix
  HPV55: in genital neoplasias and cancers of the uterine cervix condylomas and papillomas.

In a variant of the invention, the probe is combined with probes derived from other papillomaviruses, in particular those designated below: in the case of HPV49, in combination with the HPVs1, 2d, 4 or, as an alternative, in combination with the HPVs3, 10a, 10b, 28, 29, in the case of HPV50, in combination with the HPVs5, 17a, 24, or as an alternative, in combination with the HPVs5, 8, 14b, 36, in the case of HPV54, in combination with the HPVs16, 18, 33, 39, or as an alternative, in combination with the HPVs6, 11, 42, in the case of HPV55, in combination with the HPVs6, 11, 42.

Each of the probes according to the invention or the mixtures containing the above-mentioned probe can in particular be used as follows, it being naturally understood that the diagnostic assays described are not to be considered as limiting the conditions of use of the probes or mixtures of probes according to the invention.

The example under consideration relates to the identification of the HPV in a biopsy, in cells obtained by scraping lesions or in sections of biopsies fixed with the Carnoy mixture (ethanol, chloroform, acetic acid 6:3:1) and covered with paraffin. The examination requires the prior extraction of the DNA from the samples according to known methods, and involves the analysis of this DNA by molecular hybridization experiments performed under stringent or less stringent conditions with the aid of radioactive probes (labelled with $^{32}$P or $^{35}$S) prepared from the HPV according to the invention or mixtures of DNAs or HPVs.

Several methods of hybridization can be used. For example, the dot blot methods of hybridization can be employed. This method comprises depositing an aliquot of DNA on membranes (nitrocellulose or "genescreenplus") after the denaturation of the DNA, the hybridization of each membrane under normal conditions with a mixture of probes and the detection of the radioactive hybrids by contacting the membranes with a radiographic film. A blot hybridization method may also be used. This method comprises the electrophoretic separation in an agarose gel of the DNA fragments obtained after treatment of the DNA by restriction enzymes, the transfer of the fragments to membranes (nitrocellulose, "Genescreenplus") after alkaline denaturation, and their hybridization under normal conditions with different mixtures of probes. The formation of radioactive hybrids is detected after contacting the membranes with a radiographic film.

The radioactive probes consist of either the DNAs of HPVs labelled by the method of "nick-translation", or of RNAs prepared by transcription of viral DNAs inserted into a vector, for example of the SP6 type. The use of radioactive probes offers the advantage of high sensitivity but it does not exclude the use of non-radioactive probes, for example biotinylated probes capable of being recognized by antibodies either labelled or recognized by antibodies carrying an enzymatic, fluorescent, etc . . . marker.

The invention also relates to competent cell cultures transformed with recombinant DNAs of the type mentioned above, in particular, those in which the nucleotide sequence corresponding to the DNA of the papillomaviruses is placed under the control of transcription and regulatory elements of this nucleotide sequence in the said cell culture.

Consequently, it also relates to expression products of these recombinant DNAs and the corresponding antibodies capable of being produced against these, products of expression.

In this respect, the invention relates to the polypeptides resulting from the expression of genes E1, E2, E6, E7, E4, E5, L1, L2 which can thus be produced and which correspond to each of the papillomaviruses.

The procedure according to the invention for the production of these polypeptides consequently comprises the transformation of competent cell cultures with one of the recombinant DNAs, such as those defined above, so that the nucleotide sequence corresponding to one of the said proteins can be expressed in this cell host, the recovery of these polypeptides from the products synthesized by the competent cell host, and their purification (for example by contacting the expression products previously extracted from the cell cultures or the medium in which these latter were produced with antibodies formed against such polypeptides).

However, a special importance attaches to the products of expression of the L2 gene of each of the genomes of the papillomaviruses according to the invention in that they can be used for the in vivo production of antibodies capable of recognizing the expressions products of the L2 gene in biological samples infected with the corresponding papillomavirus and not by a papillomavirus of a different type, and more particularly, when the preparations of the type in question have been fixed beforehand.

The invention also relates to hybrid polypeptides containing the above-mentioned polypeptides and derivatives of the corresponding papillomaviruses, for example, the L2 protein fused with other polypeptide sequences to the extent that these latter do not bring about any essential modification of the immunogenic properties of the L2 protein. The presence of these other polypeptide fragments can result from the mode of production used for these hybrid polypeptides, by genetic engineering. For example, these hybrid polypeptides contain a sequence derived from beta-galactosidase. Such products can be obtained by transformation of E. coli with suitable vectors (phages or plasmids) modified by all or part of the lactose operon and containing in addition, inserted downstream from the promoter of the lactose operon (or any other suitable promoter, for example the lambda phage promoter), the nucleotide sequence derived from a L2 gene arising from the papillomavirus according to the invention in question. Recourse is advantageously had to plasmids or phages of this type containing at least a part of the gene of beta-galactosidase of the lactose operon.

When they have been purified, the polypeptides according to the invention can also be used in the methods of purification of the antibodies which correspond to them, in particular, purification from the sera of animals which have been immunized by these polypeptides. In particular, these polypeptides can be bound to affinity columns. The purification of the comprises passing the serum containing the antibodies through affinity columns bearing the above-mentioned polypeptides. The antibodies selectively bound to these columns can then be recovered by dissociation of the antigen-antibody complexes by means of a suitable buffer possessing an adequate ionic strength, for example, a solution of a salt such as ammonium acetate. Recourse may also be had to acidified solutions.

The invention also relates to a procedure for the production of antibodies to the said polypeptides, in particular, to the expression products of the genes E6, E7 or preferably, L2, of each of the papillomaviruses according to the invention, this procedure comprising the immunization of a suitable living host with the said polypeptides and the recovery of the antibodies formed from a serum of the immunized host. In particular, this comprises placing the sera in contact with the corresponding polypeptides in the purified state, and by the recovering the antibodies from the antigen-antibody complexes formed.

Finally, the invention relates to compositions comprising the antibodies according to invention (or groups containing these antibodies in combination with antibodies derived from other papillomaviruses), in particular, compositions containing the antibodies derived from compositions or "cocktails" of DNA-HPVs referred to earlier and to which reference will be made again in what follows (or corresponding groups of antibodies).

In particular, the invention relates to antibodies or corresponding mixtures of antibodies generally present in a given type of disease. After purification, these antibodies in combination with an appropriate pharmaceutical vehicle, can be administered, in particular, by the parenteral route, to the patient concerned in the treatment of the given disease once it has been clinically diagnosed as the result of an in vitro diagnostic assay on a histological or cytological sample taken from this patient, or as soon as an in vivo diagnostic assay has revealed the relatedness of the infectious papillomavirus to a type similar to that of one of the set of papillomaviruses mentioned above. These sera are then capable of bringing about a regression of the disease induced by the papillomavirus according to the invention.

These antibodies can be used more particularly in diagnostic assays for an infection relating to one of the papillomaviruses according to the invention or of variants of these papillomaviruses, to the extent that histological sections derived from infected people may also contain expression products of some of the structural genes, in particular L2, of these same papillomaviruses or corresponding variants.

These antibodies, possibly associated with antibodies derived from other papillomaviruses under the conditions mentioned above, can also be advantageously used for in vitro diagnosis, in particular:

HPV49: in cutaneous warts (in particular, common and plantar warts) and the differential diagnosis of epidermodysplasia verruciformis, HPV50: in epidermodysplasia verruciformis, intra-epithelial neoplasias and cutaneous cancers, HPV54: in genital neoplasias and cancers of the uterine cervix, HPV55: in genital neoplasias and cancers of the uterine cervix, condylomas and papillomas.

The invention thus also relates to an in vitro diagnostic procedure comprising contacting histopathological sections derived from lesions induced in the patients concerned by one of the papillomaviruses in contact with the chosen antibody or antibodies under conditions which enable the formation of an antigen-antibody complex and the detection of this antigen-antibody complex. Advantageously, the detection is performed on preparations fixed under dissociating conditions, for example, with the CARNOY medium or a mixture already mentioned above in the monograph by L. LISON entitled "Animal Histochemistry and Cytochemistry".

The anti-L2 antibodies which can be bound can be recognized by other antibodies formed against the former, these other antibodies bearing suitable markers, preferably non-radioactive markers. These markers are, for example, enzymatic or fluorescent in nature.

The antibodies thus selected, like the hybridization probes defined above to which they correspond, can consequently be used for the in vitro diagnosis of the corresponding types of diseases.

Finally, the invention relates to the corresponding vaccinating compositions containing one or preferably several L2 proteins in combination with a pharmaceutically acceptable vehicle suited to the chosen mode of administration, in particular, by the parentarel route, which can be used to protect those persons at high risk of suffering from a disease due to corresponding papillomavirus.

The strains of the DNA-HPVs mentioned above were deposited with the National Collection of Cultures of Microorganisms (Collection Nationale de Cultures de Microorganisms, "C.N.C.M."). Institut Pasteur, 28 rue du Docteur Rous, 75724 Paris Cedex 15, France, on 6 May 1988 under the file numbers:

PGEM 4 HPV 49: I-754

PSP 65 HPV 50: I-755

PSP 64 HPV 54: I-756

PGEM 4 HPV 55 A: I-757

PGEM 4 HPV 55 B: I-758.

The invention also relates to shorter fragments of, e.g. from 15 to 25 nucleotides, derived from the DNAs according to this invention for use in variants of hybridization methods applicable in the in vitro diagnosis of this invention. Such variant methods involve more particularly the "polymerase chain reaction" (PCR) as disclosed in U.S. Pat. Nos. 4,683, 200 and 4,683,195 and in European patent application 200,362.

We claim:

1. Isolated and essentially pure DNA having the nucleotide residue sequence of HPV 55 having Accession Numbers C.N.C.M. I-757 and I-758.

2. The isolated and essentially pure HPV 55 DNA of claim 1, wherein said DNA is labelled with a label selected from the group consisting of a radioactive marker and a non-radioactive marker.

3. A recombinant DNA comprising a cloning vector and HPV 55 DNA of claim 1.

\* \* \* \* \*